United States Patent [19]

Bielefeldt

[11] 4,190,078

[45] Feb. 26, 1980

[54] APPARATUS FOR CONVERTING OF SPIN FLOW ENERGY INTO PRESSURE ENERGY

[75] Inventor: Ernst-August Bielefeldt, Hollenstedt, Fed. Rep. of Germany

[73] Assignee: Messerschmitt-Boelkow-Blohm GmbH, Munich, Fed. Rep. of Germany

[21] Appl. No.: 801,382

[22] Filed: May 27, 1977

[30] Foreign Application Priority Data

Jun. 5, 1976 [DE] Fed. Rep. of Germany ....... 2625422

[51] Int. Cl.² .............................................. F15D 1/04
[52] U.S. Cl. ................................ 137/561 R; 137/809
[58] Field of Search ............... 137/808, 809, 810, 812, 137/813, 561 R

[56] References Cited

U.S. PATENT DOCUMENTS

| | | | |
|---|---|---|---|
| 3,515,158 | 6/1970 | Utz | 137/812 |
| 3,563,260 | 2/1971 | Ellis | 137/812 |
| 3,849,086 | 11/1974 | Johnson | 137/812 X |
| 4,003,405 | 1/1977 | Hayes | 137/810 X |

*Primary Examiner*—William R. Cline
*Attorney, Agent, or Firm*—W. G. Fasse; W. W. Roberts

[57] ABSTRACT

The present apparatus is constructed to convert or reconvert spin flow energy into pressure energy. For this purpose a conduit forms a chamber intermediate the ends of the conduit. The chamber and a flow control member operatively supported in the chamber are of rotational symmetry and so shaped that predetermined flow passage configurations are accomplished which facilitate the conversion of the spin flow into an axial flow.

11 Claims, 5 Drawing Figures

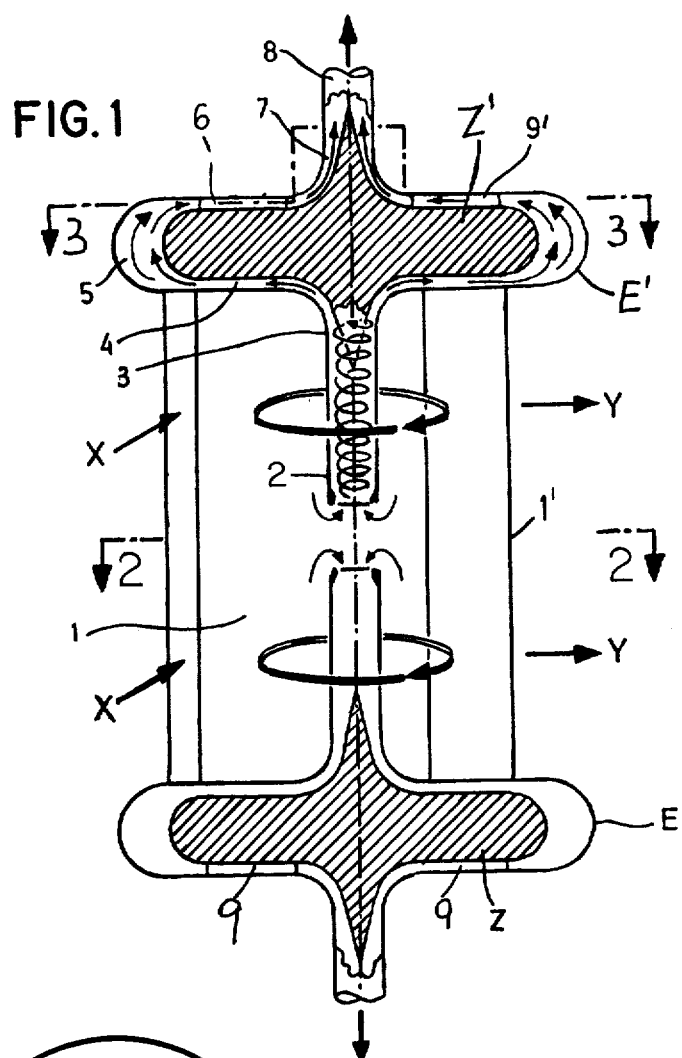
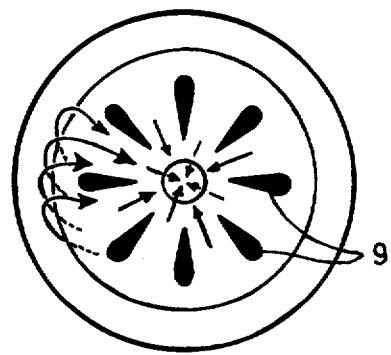
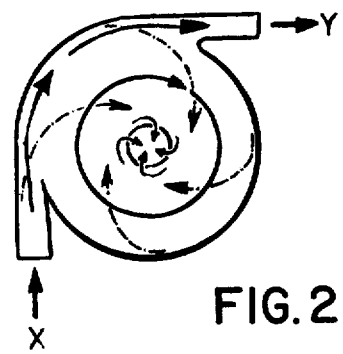

APPARATUS FOR CONVERTING OF SPIN FLOW ENERGY INTO PRESSURE ENERGY

BACKGROUND OF THE INVENTION

The present invention relates to an apparatus for converting or reconverting of spin flow energy into pressure energy.

In systems which employ centrifugal forces for the separation of materials, a type of flow emerges from the separation housing and enters into the pipe conduits, which has a spin flow component. Such spin flow component may be smaller or larger, depending on the type of system involved. Since the spin energy within the pipe conduit is lost as such, it may, under certain circumstances, be useful to recover the spin energy by means suitable for this purpose. One advantage of such recovery of the spin energy is seen in that the energy requirement of the material separation system may be substantially reduced. Thus, several different solutions for reconverting the spin energy into pressure energy have been made heretofore.

Thus, it is, for example, known to employ so-called spin diffusers. In such diffusers the spin flow is guided into a pipe of increasing cross sectional flow area. In such a pipe diffuser, the circumferential component, as well as the meridional component of the flow velocity is decelerated due to the increasing flow cross sectional area, whereby pressure energy may be recovered. However, the spin diffuser has the drawback that its flow guide characteristics are disadvantageous. Besides, the flow at the outlet port of such a spin diffuser still comprises a remainder spin. Thus, this type of diffuser is not capable to provide an immediate transition of a spin flow into a parallel flow in a pipe.

Another way of recovering the spin energy employs a spirally shaped housing. Such spin housing is substantially flat and the spin flow enters centrally into the spiral housing in a direction extending perpendicularly to the plane of the spiral and centrally thereof. The flow emerges from the spiral housing from a tangentially extending exit port. One drawback of such housings is seen in that the flow on its way from the center of the spiral to the outer wall of the spiral, is guided in a disadvantageous manner. Such disadvantageous flow or flow guide conditions cause flow losses which substantially diminish the converting efficiency of the housing. It is also disadvantageous from a construction or manufacturing point of view that the inlet channel and the outlet channel form a right angle relative to each other.

Another prior art method for recovering of spin energy employs a so-called axial guide apparatus, wherein the rotating flow in the pipe or conduit is converted or transformed into an annular flow by means of a central body. The annular or ring flow in turn is deflected into the longitudinal direction by means of guide veins arranged in ring fashion. In this manner it is possible to substantially diminish the circumferential component of the ring flow so that at the end of the central body an adequately parallel pipe flow prevails. However, this type of prior art apparatus operates with substantial losses at higher circumferential speeds because the transformation of the spin energy into pressure energy takes place in this type of apparatus along a very short flow passage. In addition, it is necessary to carefully adapt the guide vanes relative to any given operational condition due to the short length of the transformation passage. Thus, where deviations occur from the given operational condition, the apparatus operates with substantial flow losses.

OBJECTS OF THE INVENTION

In view of the above, it is the aim of the invention to achieve the following objects, singly or in combination:

to avoid the drawbacks of the prior art, more specifically, to provide a direct transition of a spin flow into a parallel pipe flow in an efficient manner;

to assure that the parallel pipe flow is available at the outlet port of the apparatus; and to assure a useful efficiency in the transformation even at higher circumferential speeds of the spin flow.

SUMMARY OF THE INVENTION

According to the invention, there is provided an apparatus for reconverting or recovering of spin flow energy. The apparatus delivers pressure energy at its exit port. For this purpose, a central body of rotational symmetry is located in a chamber, also of rotational symmetry, in a pipe conduit in such a manner that a hollow space is formed, also having a shape of rotational symmetry between the central body and the chamber. The chamber and the body are shaped in such a manner that any volume element of a medium flowing through the space encounters the following flow conditions in sequence. Starting from an inlet port the flow will first meet a smooth transition from an axially directed flow into a radially outwardly directed flow which then enters into a plate diffuser followed by an annular deflection zone merging into a guide zone causing a flow component radially inwardly which then passes through a smooth transition from the guide zone into an axial pipe flow. According to the invention, there may also be provided guide means in said guide zone, whereby the rear edges of said guide vanes are arranged in respective meridional planes of said central body.

BRIEF FIGURE DESCRIPTION:

In order that the invention may be clearly understood, it will now be described, by way of example, with reference to the accompanying drawings, wherein:

FIG. 1 illustrates an axial sectional view in a somewhat schematic manner through a centrifugal separator comprising two flow converters according to the present invention;

FIG. 2 is a sectional view through the apparatus of FIG. 1 along section line 2—2;

FIG. 3 is a schematic sectional view along section line 3—3 in FIG. 1;

Figure 4:
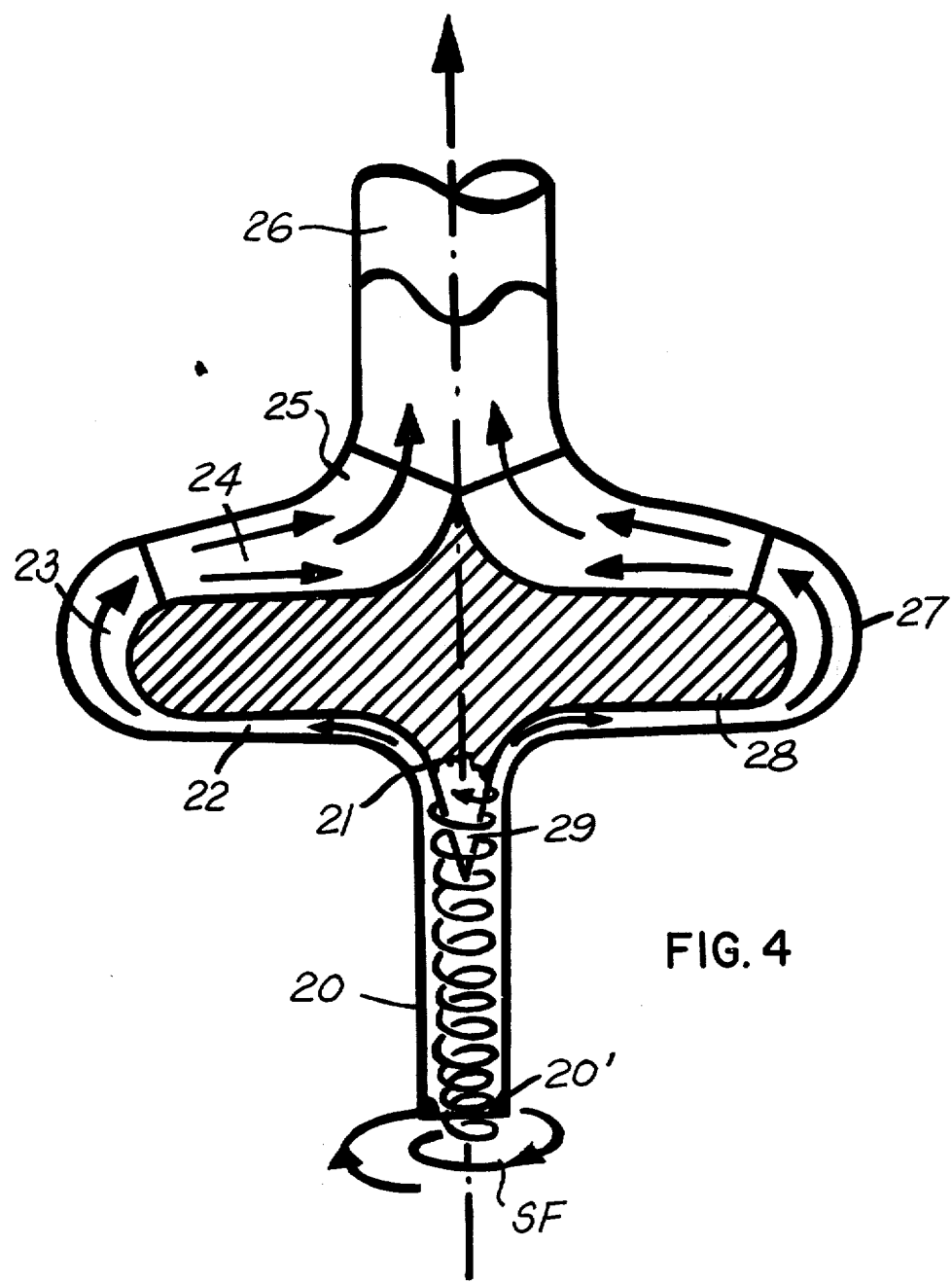
Figure 5:
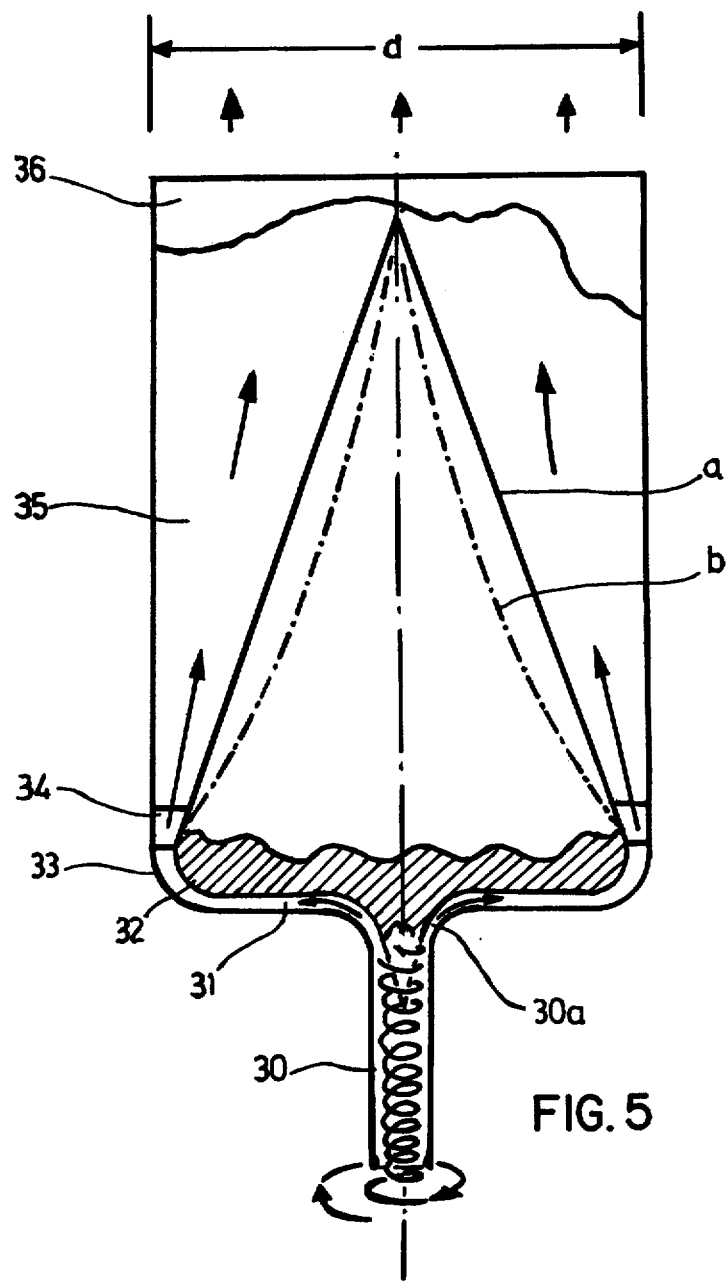

FIG. 4 is a sectional view similar to that of FIG. 1, however, illustrating a modification of the flow converter according to the invention, wherein the guide zone is provided with increasing cross sectional areas in the flow direction; and FIG. 5 is a further modification of the flow converter according to the invention, showing axially two embodiments of the central flow control body with a conical shape or with a curved conical shape.

DETAILED DESCRIPTION OF PREFERRED EXAMPLE EMBODIMENTS:

FIGS. 1 and 2 illustrate a whirling separator chamber 1 having a housing 1'. Such a separator chamber is, for example, described in German Patent Publication (DOS) No. 2,160,415. The separator is provided with two flow converters E and E'. Only one converter will be described in detail since they are identical to each other. Each converter functions in the same manner for reconverting spin energy into fresh energy. Each converter is provided with inlet port means 2 and outlet port means 8, connected through respective pipe sections or conduits to the separation chamber E or E'. Each chamber has a shape of rotational symmetry and a flow control central member or body Z, Z' is operatively positioned in its respective chamber. The rotational symmetry and size of the chambers and similarly the rotational shape and size of the central flow control bodies are selected relative to each other in such a manner that an annular flow passage is formed between the chamber and the respective central flow control body. The spin inside the separator chamber 1 is maintained or driven by the tangential flow x-y. A suction into the inlet ports 2 is also maintained.

The apparatus according to the invention may be used in all those instances where flowing media include a spin energy component, for example, in a cyclone of conventional construction.

The spin flow which has been sucked into the inlet ports 2 flows toward the central body Z, Z', whereby it first encounters a first flow passage 3 providing a smooth transition from the axial flow direction into a radially outward flow direction as shown by the arrow. A plate diffusser 4 forms a second flow passage component for the radially outwardly directed flow. An annular deflection zone 5 provides a third flow passage component which interconnects the plate difusser 4 with a further flow passage component providing a guide zone 6, which in turn merges into a fifth flow passage component 7 providing a smooth transition from the radially inward flow in the guide zone 6 to the axial flow toward the outlet port 8.

The flow inside the whirling or separator chamber 1 comprises a large spin component. This flow is sucked into the inlet ports 2 since the respective pipes are immersed into the housing 1'. The immersed inlet pipes 2 provide a relatively short axial passage for the spin flow which then passes through said smooth transisition 3 which transforms the axial spin flow into an annular spin flow with the least possible energy losses. The annular spin flow is then converted into a radially outwardly travelling flow. When travelling in the radially outward direction the spin flow enters into the plate diffuser 4, whereby already a certain pressure energy may be recovered because the radial distance has already changed relative to the diameter of the pipe conduit. Inside the plate diffuser 4 most of the spin energy is reconverted into pressure energy which is due to the reduction in the circumferential speed u as the radius r of the outward flow increases. The respective relationship is as follows:

$$u = k/r^m$$

wherein K is a constant and wherein the exponent "m" will have a value corresponding approximately to 1.

The plate diffuser 4 merges at its periphery into the deflection zone 5 which has an advantageous or rather an efficient flow dynamic configuration. The flow is further decelerated in the deflection zone 5 as it enters into said zone and as it is deflected. Besides, as the flow leaves the deflection zone 5 in a radially inwardly extending direction, the flow is somewhat accelerated resulting in small deflection losses. However, the rotational symmetry of the deflection zone 5 diminishes the flow losses in the flow field. Since at each point of the circumference the flow conditions are the same, a quasi two dimensional flow is maintained. After the deflection of the flow by 180° or about 180°, the flow enters into the guide zone 6 which is preferably provided with guide vanes 9 having rear edges arranged to face radially inwardly as best seen in FIG. 3. The rear edges of these vanes 9 are located in a respective meridional plane of central body Z,Z' and may serve for holding the flow control central body Z, Z' in position in the respective chamber E, E'.

Also as shown in FIG. 3, the radially outwardly facing front edges of the guide vanes 9 are relatively blunt. The purpose of this shape of the radially outwardly facing edges of the vanes 9 is to convert any circumferential flow speed components into radial components with a minimum of flow separation in the areas of those radially outwardly pointing edges. The guide vanes 9 may, for example, as shown, be straight in the radial direction. However, for an even more improved adaptation to special flow conditions, the guide vanes 9 may be bent in the radial direction and the bluntness or pointedness of the radially outwardly directed tips of the vanes 9 may also be adapted to particular flow conditions. The number of the vanes 9 shall not be limited to the illustrated example of FIG. 3, but will be determined by the respective construction requirements of any particular situation. As the flow leaves the guide zone 6 and the vanes 9, it enters into the transition zone 7 as a pure meridional flow relative to the central body Z,Z' and is converted into a parallel pipe flow in the exit port conduit 8.

FIG. 4 illustrates another embodiment according to the invention, for converting spin energy into pressure energy by means of an immersion pipe 20, forming an inlet port 20' for the spin flow SF, and by means of the flow passages 21, 22, 23, 24, and 25. As in the first embodiment, again a smooth transition zone 21 is formed between the housing of the converter chamber 27 and the central flow control body 28 which has a conical tip 29 as in FIG. 1 to facilitate the formation of the smooth transition area 21 which merges into a plate diffuser 22 and a deflection and deceleration chamber 23 followed by the guide zone 24 and the further transition zone 25 merging into an exit conduit 26.

Again, the flow direction is indicated by the arrows and the shape of the guide zone 24 is such that the flow cross sectional area increases in the flow direction that is in the downstream direction toward the exit port. Similarly, the deflection zone has also an increasing flow cross sectional area in the flow direction, whereby substantially no flow acceleration takes place in the deflection or deceleration chamber 23 and also not in the guide zone 24. By providing a suitable flow cross sectional area in these zones 23, 24, it is possible to maintain constant the meridional speed. Actually, it is possible to even decelerate the flow speed so that these zones 23, 24 also act as a diffuser. Here again, the shape of the guide vanes in the guide zone 24 will be adapted to the predominant flow field in this area. However, the rear edges of the guide vanes facing radially inwardly will be located in respective meridional planes of the central member to avoid any circumferential component in the outward flow. After passing through the smooth transition area 25, the flowing medium enters into the exit conduit 26 without any spin component. If desired, a so-called pipe diffuser (not shown) may be inserted in the exit conduit 26.

FIG. 5 illustrates a further embodiment according to the invention, wherein the immersion pipe 30 widens to form a smooth transition area 30a with the flow control body 37, the lower end of which is shown in section, except for its downwardly pointing conical tip. The upwardly facing end of the flow control body 37 has a conical shape indicated at "a". As a modification, the conical shape my have a curved outer surface as shown by the dashed line "b". The flow control body 37 of rotational symmetry forms with the conduit a plate diffuser 31 into which the smooth transition area 30a merges. The plate diffuser 31 merges into a deflection zone 33 followed by a guide zone 34 and a diffusion zone 35, which in turn merges into the exit conduit 36. To achieve this configuration, the exit conduit 36 is provided with a constant diameter d above the deflection zone 33. In the embodiment of FIG. 5 the flow through the flow passage components 30, 31, and 33, is the same as, for example, in FIG. 4. The guide zone 34 has an increasing flow cross sectional area in the flow direction and is provided with guide vanes as described above. The guide zone 34 merges directly into the diffuser 35 carrying a substantially axial flow. The diffuser 35 simultaneously constitutes a smooth transition between the guide zone 34 and the axial flow within the exit conduit 36. As shown, the tapering portion of the central flow control body 32 has a conical shape "a". However, the efficiency of the diffuser 35 may be increased by giving the central flow control body 32 an outer conical, curved contour "b" as shown by the respective dashed line in FIG. 5.

It is efficient to place the guide vanes into a zone with a relatively low flow velocity because the deflection or guide losses at the vanes increase with the square of the increasing flow velocity v. All described embodiments of the invention take this into account. The deflection or guide losses may further be reduced by arranging the guide vanes 9 in a zone of accelerated flow, that is, in a zone having a negative pressure gradient as is the case, for example, in the embodiment of FIG. 1. Thus, flow losses due to flow separation are substantially eliminated. Under certain conditions it may be suitable to tolerate a certain proportion of spin energy in the flow emerging from the converter, whereby the structural requirements are substantially simplified. For example, it is possible to omit the guide vanes altogether.

In such an embodiment, the central flow control body would simply be secured to the walls of the chamber.

Although the invention has been described with reference to specific example embodiments, it will be appreciated, that it is intended to cover all modifications and equivalents within the scope of the appended claims.

What is claimed is:

1. An apparatus for recovering spin flow energy wherein a spin flow is converted into a parallel flow, comprising conduit means having inlet port means for said spin flow and outlet port means for said parallel flow, chamber means located in said conduit means intermediate said inlet port means and said outlet port means and having a configuration of rotational symmetry, a central member also having a shape of rotational symmetry operatively supported in said chamber means, said central member and said chamber means being dimensioned and shaped relative to each other so as to include the following flow passage components therebetween, a first flow passage component providing a smooth transition from an axial flow direction into a substantially radially outward flow direction, a second flow passage component operatively connected to said first flow passage component and constituting a plate diffuser, a third flow passage component operatively connected to said second flow passage component and constituting an annular deflection zone, a fourth flow passage component operatively connected to said third flow passage component and forming a guide zone to cause a substantially inward flow direction, and a fifth flow passage component operatively connected to said fourth flow passage component and constituting a smooth transition from said inward flow direction into an axial flow direction toward said outlet port means whereby said flow passage components are arranged in the recited sequence as viewed in the flow direction from said inlet port means to said outlet port means.

2. The apparatus of claim 1, further comprising guide means operatively positioned in said guide zone.

3. The apparatus of claim 2, wherein said guide means include guide vanes having rear edges located in respective meridional planes of said central member.

4. The apparatus of claim 2, wherein said guide means comprise guide vanes having such a shape that the flow cross sectional area within said guide zone diminishes in the downstream direction toward said outlet port means.

5. The apparatus of claim 2, wherein said guide means comprise guide vanes having such a shape that the flow cross sectional area within said guide zone remains substantially constant in the downstream direction over a given length of said guide zone.

6. The apparatus of claim 2, wherein said guide means comprise such a shape that the flow cross sectional area increases in the downstream direction.

7. The apparatus of claim 1, wherein said guide zone comprises a flow cross sectional area which diminishes in the downstream direction.

8. The apparatus of claim 1, wherein said guide zone comprises a flow cross sectional area which remains substantially constant in the downstream direction over a given length of said guide zone.

9. The apparatus of claim 1, wherein said guide zone comprises a flow cross sectional area which increases in the downstream direction.

10. The apparatus of claim 1, wherein said central member has a substantially conical extension pointing toward said outlet port means, said conical extension and said conduit means forming diffuser means, said guide zone merging directly into said diffuser means.

11. The apparatus of claim 10, wherein said substantially conical extension of said central member has a curved outer contour.

* * * * *